United States Patent [19]
Apgar

[11] Patent Number: 5,984,925
[45] Date of Patent: *Nov. 16, 1999

[54] LONGITUDINALLY ADJUSTABLE BONE PLATES AND METHOD FOR USE THEREOF

[75] Inventor: Mark E. Apgar, Columbus, Ohio

[73] Assignee: Cross Medical Products, Inc., Irvine, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/902,710

[22] Filed: Jul. 30, 1997

[51] Int. Cl.$^6$ ..................................... A61B 17/56
[52] U.S. Cl. ................... 606/69; 606/70; 606/71
[58] Field of Search ................ 606/69, 70, 71, 606/72, 73, 61, 60

[56] References Cited

U.S. PATENT DOCUMENTS

| | | | |
|---|---|---|---|
| 4,493,317 | 1/1985 | Klaue | 606/69 |
| 4,573,458 | 3/1986 | Lower . | |
| 4,771,767 | 9/1988 | Steffee . | |
| 4,905,679 | 3/1990 | Morgan . | |
| 5,139,497 | 8/1992 | Tilghman et al. | 606/69 |
| 5,190,544 | 3/1993 | Chapman et al. | 606/69 |
| 5,336,224 | 8/1994 | Selman . | |
| 5,413,577 | 5/1995 | Pollock . | |
| 5,415,661 | 5/1995 | Holmes . | |
| 5,423,826 | 6/1995 | Coates et al. . | |
| 5,468,242 | 11/1995 | Reisberg | 606/69 |
| 5,569,250 | 10/1996 | Sarver et al. | 606/69 |
| 5,578,036 | 11/1996 | Stone et al. | 606/69 |
| 5,591,169 | 1/1997 | Benoist | 606/69 |
| 5,690,631 | 11/1997 | Duncan et al. | 606/69 |
| 5,752,958 | 5/1998 | Wellisz | 606/69 |

FOREIGN PATENT DOCUMENTS

| | | |
|---|---|---|
| 0 654 250 A1 | 5/1995 | European Pat. Off. . |
| 90 16 507 U | 4/1991 | Germany . |
| 4425 441 A1 | 3/1995 | Germany . |

*Primary Examiner*—Michael Buiz
*Assistant Examiner*—Lien Ngo
*Attorney, Agent, or Firm*—Hudak & Shunk Co., L.P.A.

[57] ABSTRACT

The invention relates to a bone plate having at least two and up to ten rimmed eyelets for receiving anchoring bone screws in a modified ball-and-socket joint. The eyelets are longitudinally aligned and joined to neighboring eyelets by curvilinear, bendable ribs extending between pairs of eyelets. The ribs are of a longer length than the distance between the external surfaces of adjacent rings which allows the longitudinal spacing of the rings to be increased or decreased by bending the ribs.

12 Claims, 3 Drawing Sheets

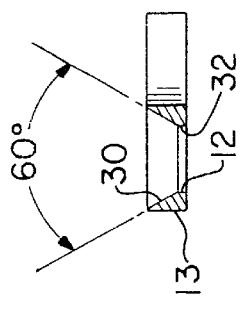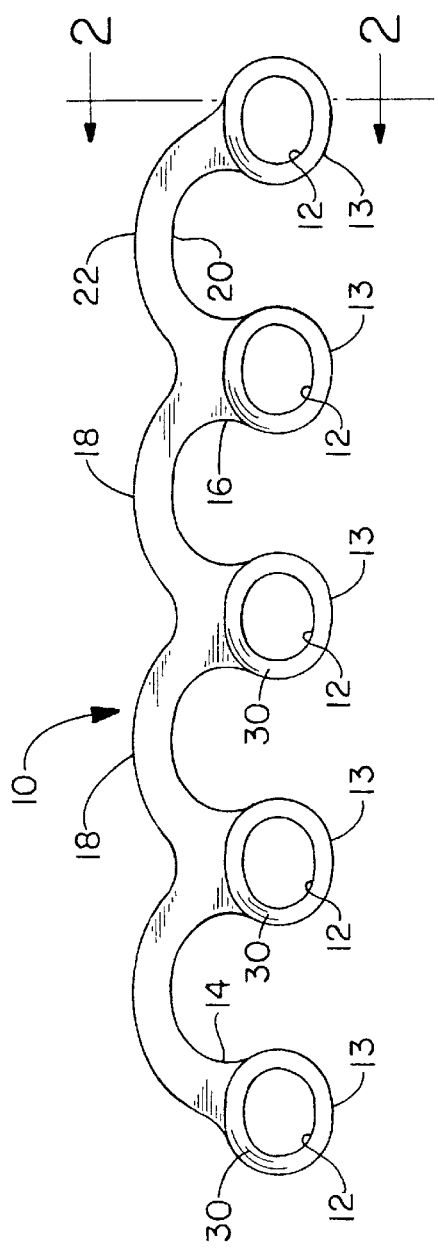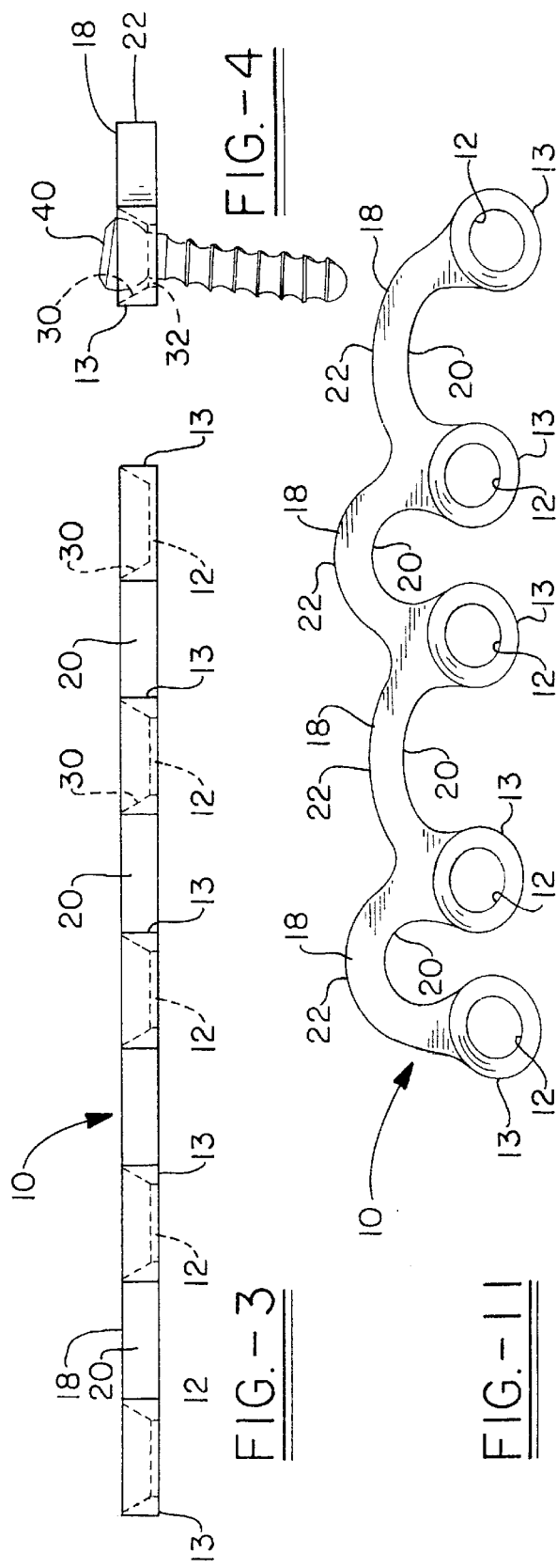

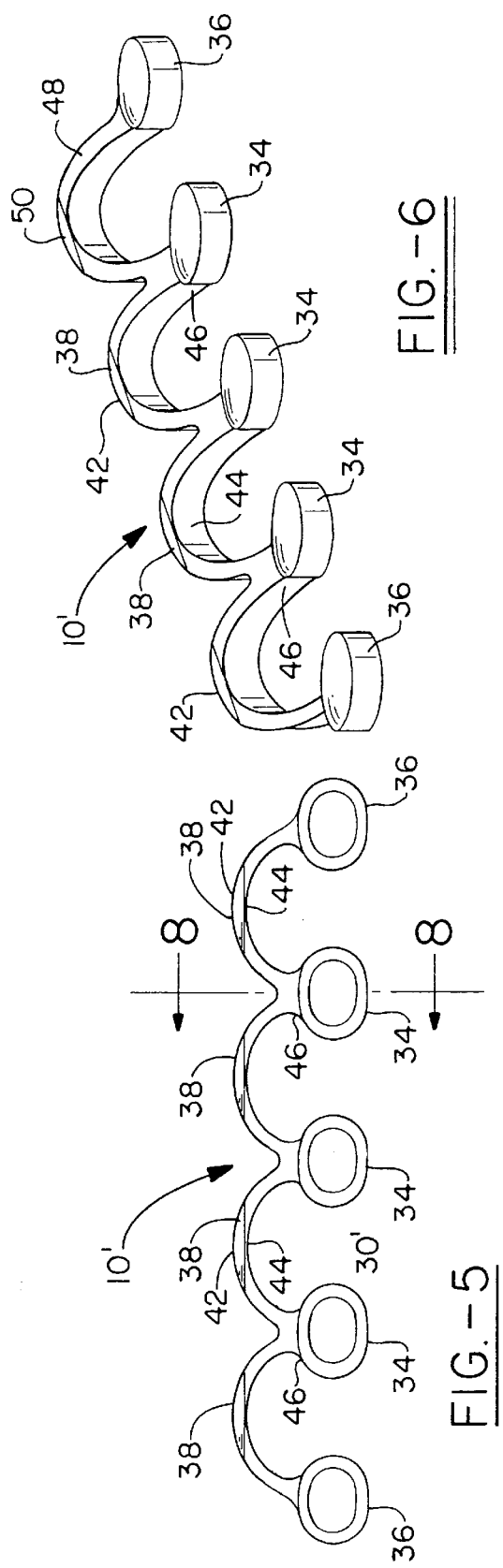
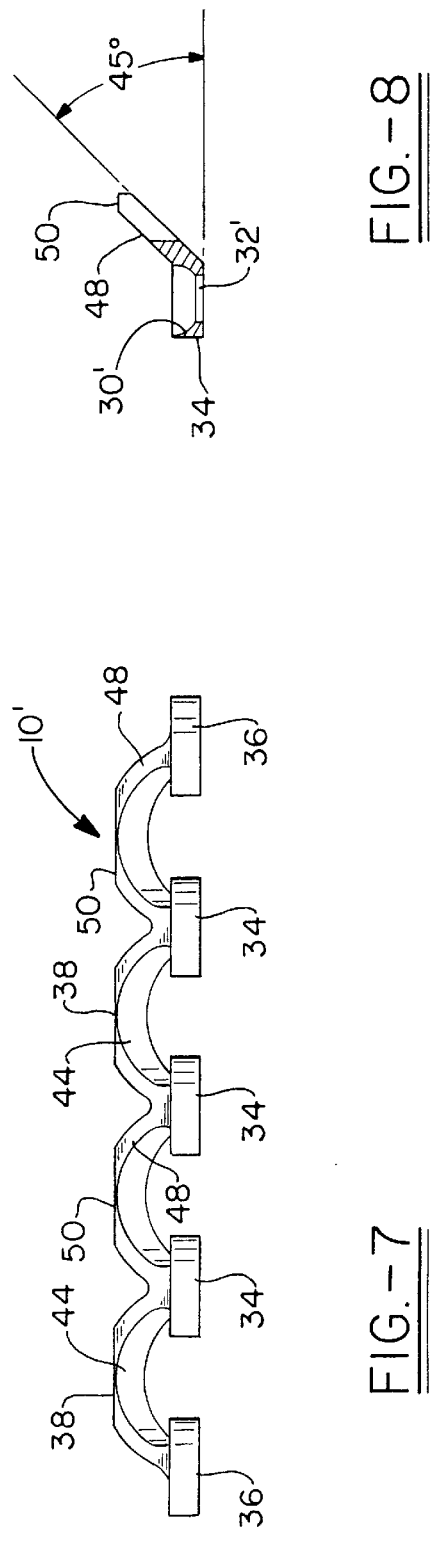

LONGITUDINALLY ADJUSTABLE BONE PLATES AND METHOD FOR USE THEREOF

FIELD OF INVENTION

The invention relates generally to a plate used for bone stabilization and more particularly to plates having means to adjust the spacing between points of attachment to the bone or bones along the longitudinal axis.

BACKGROUND OF INVENTION

Orthopaedic implants have long been used for the stabilization of bones. For example, plates have been used in conjunction with screws on long bones, and screws and hooks have been used in conjunction with rod seats and rods in the spine as a method of treating traumatic injuries as well as to correct severe misalignments such as scoliosis.

While plates have the advantage of simplifying assembly during surgical implantation, traditional applications of plates have not been as flexible as other means of fixation such as rods and anchors due to the fact that plates do not allow for longitudinal variation of the spacings at the fixation site. For some sites or bone conditions, the exact location for fixation may be limited and in such instances it is extremely advantageous to be able to readily adapt to the site by reshaping a plate and also to be able to vary the angle of entry of the anchoring screw(s) or other anchoring means.

It is therefore an object of the present invention to provide a fixation or stabilization plate for surgical implantation in humans or other animals wherein the location of the anchoring sites along the longitudinal axis can be varied by increasing or decreasing the distance.

It is a further object of the invention to provide a bone plate in which the alignment of the fixation sites along the longitudinal site can be varied.

It is a further object of the invention to provide a plate having fixation sites which enable variation in the angle of entry of an anchor such as a bone screw.

BRIEF DESCRIPTION OF DRAWINGS

FIG. 1 is a top plan view of a first embodiment of a bone plate in accordance with the invention;

FIG. 2 is a cross-sectional view taken along lines 2—2;

FIG. 3 is a side view of the plate of FIG. 1;

FIG. 4 is an end view of the plate in accordance with FIG. 1;

FIG. 5 is a top view of a second embodiment of the invention;

FIG. 6 is perspective view of the plate in accordance with the invention;

FIG. 7 is a side view of the plate of FIG. 5;

FIG. 8 is a cross-sectional view of the second embodiment of the invention taken along lines 8—8 of FIG. 5;

FIG. 11 is a top view of the first embodiment of the invention which has been bent to accommodate a different spacing.

DETAILED DESCRIPTION OF INVENTION

Figure 9:
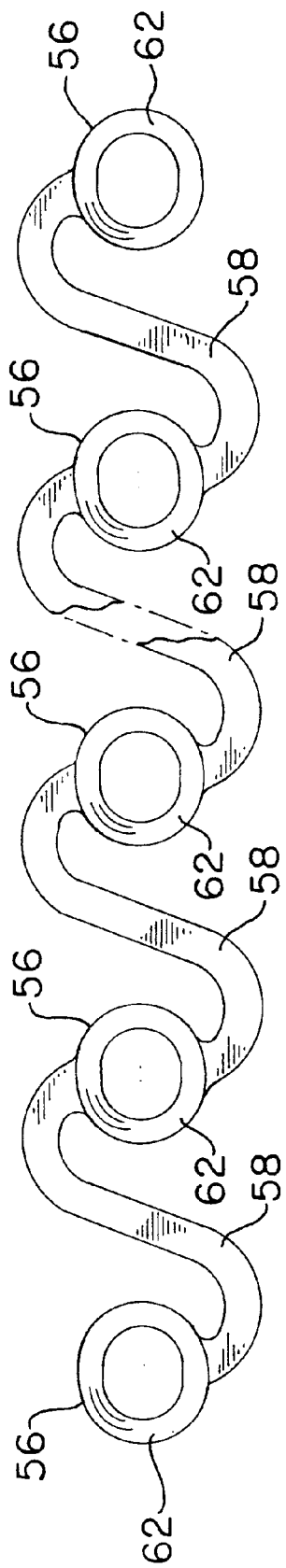
FIG. 9 is a top view of a third embodiment of the invention.

A plate in accordance with the invention is illustrated generally at 10 in FIG. 1. An unaltered plate (i.e., prior to site-specific bending) includes a series of anchoring sites or holes, i.e., eyelets 13 (or rimmed holes for receiving bone screws), which are longitudinally aligned and which are intended to receive an anchoring element such as, for example, a bone screw 40, in order to anchor the plate 10 to an appropriate bone or bones. Of course, other anchoring means could be used such as a pin, rivet, wedge, and/or cement or the like. The eyelets are connected by a sinuous, bendable structure or rib 18 characterized in that it does not include a linear portion which is longitudinally aligned with the long axis of the plate and, in fact, includes repeating "C" shapes or "S" shapes so that no linear longitudinally aligned structure exists. As used herein, longitudinal axis refers to an imaginary axis at the center of the plate which extends in the long direction of the plate; the actual connecting portion of the plate may be offset. The ribs may include a linear portion which diagonally transverses the long axis or may arch between eyelets leaving a space or void along the longitudinal axis between eyelets Thus it can be seen that the rib is longer than the longitudinal distance between eyelets which enables this distance to be varied by bending the ribs such as is in FIG. 11. The plate can be used on the spine, for example on the sacrum, or on larger bones such as the pelvis, or on long bones.

Each eyelet 13 includes a recessed portion 30 which forms an angle of about 30° on either side of a line perpendicular to the longitudinal axis, for a total angle of 60° as illustrated in FIG. 2. The recessed portion 30 terminates in an oval-shaped through bore 12. The eyelet has a 60° angle on its internal slope. The slot is from about 4 to about 5 mils, and preferably about 5.3 mils long, and from about 4 to about 5 mils, and preferably about 4.3 mils wide. The bore 12 includes a necked portion 32 which secures the rounded, bottom portion of a head of an anchoring screw 40 as illustrated in phantom in FIG. 4. This cooperation forms a limited ball and socket joint. The ovoid or elongated shape, along with the narrower necked portion, allows the screw 40 to be implanted at various angles of insertion to best access the anchoring site.

The eyelets 13 are connected by a series of arched ribs 18 having a smooth external radius 22 and internal radius 20 joining together at adjacent eyelets to provide a necked portion 16. The ribbed portion can be bent to enable the distance between neighboring eyelets to be varied and more particularly to enable a shorter or longer distance between the eyelets and specifically between the points of fixation. A preferred standard distance (for an unaltered plate) is 16 millimeters between the center of each eyelet; however, manipulation of the plate can allow an increase of up to 18 to 20 millimeters or, conversely, the distance can be collapsed down to 10 millimeters (i.e., a distance of around 9 millimeters between the central longitudinal axes of the screws). Manipulation of the plate allows elongation or an increase in the distance between slots of about 2 to about 4 mils or, alternatively, the slots can be compressed until the external diameters are touching.

Preferably the ribs 18 have a smooth radius for better stress distribution and better biocompatibility.

The plate is from about 1.5 to 4 mils, preferably about 2 to 3.5 mils, and most preferably about 2.5 mils in thickness to resist axial loading. It is preferred that the plate will be made of a suitable surgical material such as surgical-grade stainless steel or titanium and will deform (i.e., can be longitudinally compressed or expanded) in excess of 40 pounds of force using a spreader compressor.

The curve 20 used on the inside radius of the rib has a radius of from about 5.5 to about 7 mils. The outside radius is from about 8 to about 10 mils, each radius being ±2 mils and preferably ±1 mil, that is, about 6 to about 7 mils on the inside, and about 8.5 to about 9.5 mils on the outside.

The plate may include as few as one linkage, i.e., one rib and two eyelets, or may include as many as nine linkages, but preferably includes four to seven linkages, i.e., five eyelets and four ribs, six eyelets and five ribs, or seven eyelets and six ribs.

A second embodiment of the invention is shown in FIGS. 5–8. Again, the plate 30 comprises a series of eyelets 34 connected by a series of arched ribs 38 having a smooth external radius 42 and internal radius 44. Again the ribs 38 joining the intermediate eyelets 34, i.e. excluding the first and last eyelet 36, come together to form a necked area 46. The ribs are configured substantially as described above and again include elongated slots having sloped sides to permit variable angulation of the anchoring screw or other anchoring means. This embodiment includes a lateral rise 48 in the curved rib portion to allow for variations in bone topography. The rib may include an angle, as illustrated in FIG. 8, of from about 15° to about 60°, and preferably about 45°+10°. It is preferred that the overall height be restricted to about 7 to about 8 mils, and that the top portion of the rib include a flat 50 in order to avoid a sharp edge on the top.

The plates in embodiments 1 and 2 may be used in tandem to provide symmetry in use. For example, two of the same plate may be used together with opposing eyelets or alternatively opposing ribs.

Figure 10:
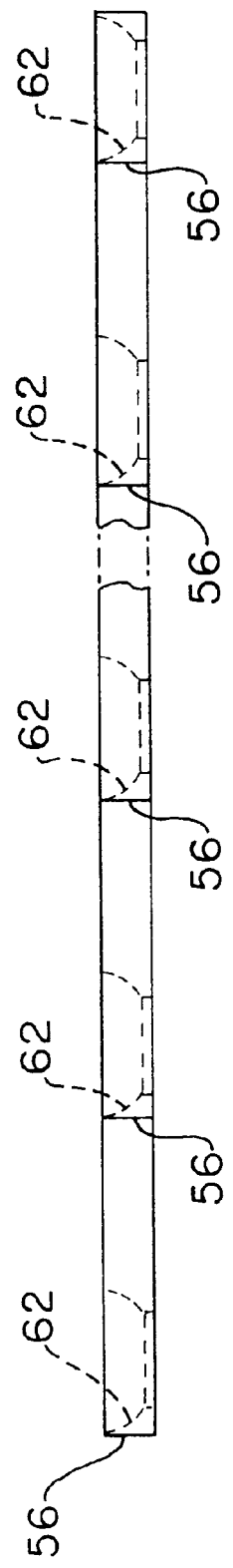
FIG. 10 is a side view of the embodiment shown in FIG. 9 illustrating the anchor holes in phantom.

FIGS. 9 and 10 represent a third laterally symmetrical embodiment having similar eyelets 56 with elongated slots 62. The eyelets 56 are connected by ribs 58 having inward and outward curves (i.e., forming a gentle "S" shape transversing the longitudinal axis and curing beyond the outer rim of the eyelets on either side). The curved S-shaped ribs 58 which connect the eyelets 56 extend both below and above the longitudinal axis. The embodiment may expand from about 16 to about 21 mils and collapse to about 9 mils. This embodiment is planar. The location of the eyelets can be changed by bending the ribs to alter the relative spacing.

FIG. 11 illustrates how a plate (as shown in FIG. 1) can be bent in order to accommodate an irregular spacing.

While in accordance with the patent statutes the best mode and preferred embodiment has been set forth, the scope of the invention is not limited thereto, but rather by the scope of the attached claims.

What is claimed is:

1. A linearly extending bone plate having a longitudinal axis, comprising:

at least two eyelets having through holes, said eyelets being aligned along said longitudinal axis and being joined by a bendable curvilinear shaped rib having a length which exceeds the distance along said longitudinal axis between said eyelets, said distance being from about 10 to 20 millimeters, whereby the longitudinal distance between said eyelets can be made smaller or larger by bending said rib and said bending requiring a force in excess of 40 pounds.

2. A bone plate as set forth in claim 1, wherein said eyelets each include a recess terminating in a through hole having a smaller diameter than said recess so as to form a necked area.

3. A bone plate as set forth in claim 2, wherein said through hole is elongated in the direction of the longitudinal axis.

4. A bone plate as set forth in claim 3, wherein said recess has an internal wall forming an angle of from about 15° to about 75° with respect to a perpendicular line through said hole.

5. A bone plate as set forth in Claim 1, wherein said rib has a "C" shape or "S" shape.

6. A bone plate as set forth in claim 5, wherein said bone plate includes from five to seven eyelets.

7. A bone plate as set forth in claim 6, wherein said bone plate is made from surgical-grade steel or titanium.

8. A bone plate as set forth in claim 5, wherein said eyelets include bone-contacting surfaces which substantially define a plane and said rib includes a rise above said plane.

9. A bone plate having a longitudinal axis comprising from two to ten eyelets, each of which includes a ring having an internal recess terminating in a necked area defining an elongated through hole, said rings being aligned only along the longitudinal axis and the necked area adjoining adjacent eyelets having an axis substantially perpendicular to the longitudinal axis of the plate, each of two adjacent eyelets being joined by a bendable curvilinear rib whereby the distance of said through holes along said longitudinal axis can be decreased or increased by bending said rib.

10. A bone plate as set forth in claim 9, wherein said rib has a "C" shape or "S" shape.

11. A bone plate as set forth in claim 10, wherein said bone plate includes from five to seven eyelets.

12. A bone plate as set forth in claim 11, wherein said bone plate is made from surgical-grade steel or titanium.

* * * * *